(12) United States Patent
Shah

(10) Patent No.: US 10,537,519 B2
(45) Date of Patent: Jan. 21, 2020

(54) COMPOSITIONS FOR TREATING INFECTIONS

(71) Applicant: Sci-Chem International Pty Ltd, Sydney (AU)

(72) Inventor: Aiyaz A Shah, Sydney (AU)

(73) Assignee: Sci-Chem International Pty Ltd, Sydney (AU)

( * ) Notice: Subject to any disclaimer, the term of this patent is extended or adjusted under 35 U.S.C. 154(b) by 0 days.

(21) Appl. No.: 15/678,370

(22) Filed: Aug. 16, 2017

(65) Prior Publication Data

US 2019/0054011 A1 Feb. 21, 2019

(51) Int. Cl.

| *A61K 31/045* | (2006.01) |
|---|---|
| *A61K 31/047* | (2006.01) |
| *A61K 31/125* | (2006.01) |
| *A61K 31/355* | (2006.01) |
| *A61K 9/00* | (2006.01) |
| *A61K 9/08* | (2006.01) |
| *A61K 33/34* | (2006.01) |
| *A61K 36/28* | (2006.01) |
| *A61K 36/38* | (2006.01) |
| *A61K 36/886* | (2006.01) |
| *A61K 47/10* | (2017.01) |
| *A61K 47/26* | (2006.01) |

(52) U.S. Cl.
CPC .............. *A61K 9/0014* (2013.01); *A61K 9/08* (2013.01); *A61K 31/045* (2013.01); *A61K 31/047* (2013.01); *A61K 31/125* (2013.01); *A61K 31/355* (2013.01); *A61K 33/34* (2013.01); *A61K 36/28* (2013.01); *A61K 36/38* (2013.01); *A61K 36/886* (2013.01); *A61K 47/10* (2013.01); *A61K 47/26* (2013.01); *A61K 9/006* (2013.01)

(58) Field of Classification Search
CPC .. A61K 31/045; A61K 31/047; A61K 31/125; A61K 31/355; A61K 9/00; A61K 9/08; A61K 33/34; A61K 36/28; A61K 36/38; A61K 36/886
See application file for complete search history.

(56) References Cited

U.S. PATENT DOCUMENTS

| 2003/0180347 A1 | 9/2003 | Young et al. |
|---|---|---|
| 2006/0024339 A1 | 2/2006 | Murad |
| 2006/0105055 A1 | 5/2006 | Marenick et al. |
| 2011/0064826 A1 | 3/2011 | Spurge |
| 2012/0027891 A1 | 2/2012 | Tobin et al. |
| 2012/0301409 A1 | 11/2012 | Jensen et al. |

FOREIGN PATENT DOCUMENTS

| AU | 37235/89 | 4/1990 |
|---|---|---|
| CN | 103083713 | 5/2013 |
| CN | 103156788 | 6/2013 |
| WO | 2004019885 | 11/2004 |

OTHER PUBLICATIONS

Sego, Clinical Advisor (Alternative Meds Update, Lemon Balm, Mar. 4, 2009).*

Chang, "Generic Development of Topical Dermatologic Products; Formulation Development, Process Development, and Testing of Topical Dermatologic Products," The AAPS Journal, vol. 15, No. 1, Jan. 2013.

Notification of Transmittal of the International Search Report and the Written Opinion of the International Searching Authority, or the Declaration of International Application No. PCT/AU2018/050012 dated Mar. 1, 2018.

Material Safety Data Sheet—MSDS—Natures Organics Australian Pure Sorbolene.

* cited by examiner

*Primary Examiner* — Zohreh A Fay

(74) *Attorney, Agent, or Firm* — K&L Gates LLP

(57) ABSTRACT

The present invention relates to compositions and in particular to compositions for treating a skin or mucosal membrane infection.

25 Claims, 4 Drawing Sheets

FIG. 1

| Ingredient | %w/w |
|---|---|
| Glycerol | 40 |
| Cupric sulphate pentahydrate | 3 |
| Camphor tablets | 3 |
| Isopropyl alcohol | 35 |
| PEG400 | 5 |
| Polysorbate 80 | 0.2 |
| Vitamin E | 0.1 |
| Glycerol | To 100 |

FIG. 2

| Ingredient | %w/w |
|---|---|
| Glycerol | 40 |
| Cupric sulphate pentahydrate | 3 |
| Aloe Vera 200:1 | 0.01 |
| Camphor tablets | 3 |
| Isopropyl alcohol | 35 |
| PEG400 | 5 |
| Polysorbate 80 | 0.2 |
| Vitamin E | 0.1 |
| Hypericum perforatum extract | 0.05 |
| Calendula officinalis extract | 0.05 |
| Glycerol | To 100 |

FIG. 3

| Terpenoid/Essential oil | %w/w |
|---|---|
| Menthol | 1-4 |
| Tea tree oil | 1-4 |
| Eucalyptus oil | 1-4 |

FIG. 4

| Ingredients | 1 | 2 | 3 | 4 | 5 | 6 | 7 | 8 | 9 | 10 | 11 |
|---|---|---|---|---|---|---|---|---|---|---|---|
| | %w/w | | | | | | | | | | |
| Glycerol | 40 - 60 | 42 - 62 | 44 - 64 | 46 - 66 | 48 - 68 | 49 - 69 | 50 - 70 | 51 - 72 | 52 - 72 | 50 - 70 | 40 - 60 |
| Copper Salt (Cupric sulphate pentahydrate) | 2.5 | 2.6 | 2.7 | 2.8 | 2.9 | 3.0 | 3.1 | 3.5 | 3.5 | 3.6 | 2.5 |
| Camphor | 2.5 | 2.6 | 2.7 | 2.8 | 2.9 | 3.0 | 3.1 | 3.5 | 3.5 | 3.6 | 2.5 |
| Isopropyl alcohol | 20 - 45 | 21 - 44 | 22 - 42 | 24 - 40 | 26 - 38 | 25 - 37 | 26 - 36 | 28 - 34 | 30 - 34 | 30 - 34 | 20 - 45 |
| Polysorbate 80 | 0.1 | 0.2 | 0.3 | 0.4 | 0.5 | 0.6 | 0.2 | 0.2 | 0.3 | 0.2 | 0.1 |
| Vitamin E | 0.1 | 0.2 | 0.3 | 0.4 | 0.5 | 0.6 | 0.4 | 0.3 | 0.4 | 0.3 | 0.1 |
| Calendula officinalis extract | 0.01 | 0.02 | 0.03 | 0.04 | 0.05 | 0.06 | 0.04 | 0.03 | 0.04 | 0.03 | 0.00 |
| Aloe vera | 0.1 | 0.2 | 0.3 | 0.4 | 0.5 | 0.6 | 0.4 | 0.4 | 0.3 | 0.2 | 0.00 |
| Hypericum perforatum extract | 0.01 | 0.02 | 0.03 | 0.04 | 0.05 | 0.06 | 0.04 | 0.02 | 0.03 | 0.02 | 0.00 |
| PEG400 | 1.0 | 2.0 | 3.0 | 4.0 | 5.0 | 6.0 | 5.0 | 4.0 | 5.0 | 6.0 | 1.0 |
| Menthol | 0.1 | - | 0.2 | - | 0.1 | 0.2 | - | 0.1 | 0.2 | 0.3 | 0.2 |
| Water / Glycerol | to 100 | to 100 | to 100 | to 100 | to 100 | to 100 | to 100 | to 100 | to 100 | to 100 | to 100 |

COMPOSITIONS FOR TREATING INFECTIONS

FIELD OF THE INVENTION

The present invention relates to compositions and in particular to compositions for treating a skin or mucosal membrane infection.

BACKGROUND OF THE INVENTION

Any discussion of the prior art throughout the specification should in no way be considered as an admission that such prior art is widely known or forms part of the common general knowledge in the field.

Microorganisms and viruses are responsible for a variety of diseases and disorders in humans and animals, including many dermatological disorders. Dermatophytes, for example, are a group of fungi that cause skin diseases in animals and humans. They include the genera *Microsporum, Epidermophyton* and *Trichophyton*. Tinea is a term used to describe a variety of skin mycoses including tinea pedis (commonly referred to as "athlete's foot"), tinea corporis (infections of the trunk, arms and legs), tinea manuum (infections of the finger webs), tinea cruris (infections of the groin), tinea barbae (infections of the neck) and tinea capitis (infections of the scalp).

Viruses are also responsible for a number of skin infections in animals and humans. Skin lesions such as warts, cold sores and shingles are often caused by viral infections. Most primary viral infections arise from one of three groups of viruses; poxviruses (poxviridae), herpesviruses (herpesviridae) and human papillomaviruses (papillomaviridae).

Common warts are a benign form of tumour typically caused by human papillomaviruses (HPV). Some strains of HPV, however, are also etiological agents in dysplasia and carcinomas in the oral and genital mucosa.

*Molluscuum contagiosum* is a type of poxvirus that causes skin lesions, sometimes referred to as water warts. Water warts are characterised by small, discrete, lobulated epidermal outgrowths that occur at various locations on the body.

Herpes zoster, commonly referred to as shingles, is a skin lesion caused by infection from the herpesviridae family of viruses. Shingles is often characterised by a painful rash and localised blistering which can last for several months.

Herpes Simplex Type 1 (HSV1) and Herpes Simplex Type 2 (HSV2) are etiological agents of cold sores and genital herpes, respectively. However, both types of herpes simplex virus (HSV) can be present on the mouth and genital areas, and it is possible for an individual to be infected by both HSV1 and HSV2. Infection by one strain does not render an individual immune to the other.

Recurrent outbreaks of HSV often follow a staged progression involving prodrome, vesicle formation, ulceration, crusting and healing. Prodrome is typically characterised by a short period of tingling, itching, numbness or burning with no clearly visible indication of an infection or outbreak. Vesicle formation involves the development of fluid-filled blisters, often in a cluster, and usually surrounded by sore, red skin. Ulceration occurs when the blisters open to form painful ulcers or open sores often with a yellow crust at the edges of the sore. At the crusting stage, weeping sores or ulcers are covered by a crust or scab. Healing involves the disappearance of the crust, swelling, pain and itching. Skin eruptions caused by viral infection, particularly HSV, generally have a normal infective course that lasts from between 10 and 60 days depending on the species of infective virus and the anatomical location of the infection.

After an initial outbreak of HSV, the virus may lie dormant in the skin or in nerve tissue until triggered to cause a new eruption or site infection. Triggers may include stress, fever, sunlight, hormonal changes or certain foods or drugs. When the virus is reactivated, it typically causes a sore at the site where it first entered the body.

Presently, there is no effective vaccine to prevent herpes infection. Moreover, the ability of the herpes virus to retreat into the nervous system makes it difficult to eliminate from the body. Systemic treatment of viral and fungal infections, although effective in some cases, may be associated with health risks including cardiac or hepatic toxicity, nausea, headaches and adverse drug interactions. Physical treatments such as cryotherapy, laser therapy and surgical removal, while also effective in some cases, can be painful and distressing, particularly for children, and may increase the likelihood of scar tissue formation. Topical antiviral formulations have also been developed, however, many suffer from problems such as poor stability leading to limited shelf-life, susceptibility to freezing, poor active ingredient solubility or inefficient delivery of the active ingredient.

In this context, there is a need for alternative methods and compositions for treating skin and mucosal membrane infections, and in particular, infections caused by viruses and fungi. It is an object of the present invention to overcome or ameliorate at least one of the disadvantages of the prior art or to provide a useful alternative.

SUMMARY OF THE INVENTION

In a first aspect, the present invention provides a composition for treating a skin or mucosal membrane infection the composition comprising:
 glycerol;
 at least one surfactant;
 an alcohol;
 a terpene or terpenoid compound; and
 a copper compound.

The terpene or terpenoid compound may be present in or extracted from an essential oil.

The essential oil may be obtained from a camphor laurel tree, a kapur tree, a rosemary plant, a mint plant, a eucalyptus tree or a tea tree.

Preferably, the terpene or terpenoid compound is camphor.

In one or more embodiments, the terpene or terpenoid compound is menthol.

In further embodiments, the terpene or terpenoid compound is camphor or menthol.

In another embodiment, the composition comprises camphor and menthol.

The copper compound is preferably selected from the group consisting of copper gluconate, copper carbonate, copper sulphate, copper chloride and copper salicylate.

The copper compound may be copper sulphate. Preferably, the copper sulphate is copper sulphate pentahydrate.

In one or more embodiments, the alcohol is isopropyl alcohol.

The composition may further comprise *Hypericum perforatum* extract.

The composition may further comprise *Calendula officinalis* extract.

In one or more embodiments, the composition further comprises aloe vera.

Preferably, the composition further comprises vitamin E.

The at least one surfactant preferably comprises polyethylene glycol.

The at least one surfactant may comprise polysorbate 80.

In one or more embodiments, the composition comprises substantially no water.

In another aspect, the present invention provides a method of producing a composition comprising the steps of:
i) combining glycerol and a copper compound to produce a glycerol solution;
ii) dissolving a terpene or terpenoid compound in an alcohol to produce an alcohol solution;
iii) combining the glycerol solution and the alcohol solution; and
iv) adding at least one surfactant.

Step i) preferably includes heating the glycerol solution to about 80° C.

Preferably, step i) further comprises adding aloe vera to the glycerol solution.

In one or more embodiments, step iv) further comprises adding vitamin E, *Hypericum perforatum* extract and *Calendula officinalis* extract.

In another aspect, the present invention provides a method of treating a skin or mucosal membrane infection comprising topically applying the composition of the first aspect to the skin or mucosal membrane infection.

The skin or mucosal membrane infection may be caused by a bacterium, a virus or a fungus.

Preferably, the skin or mucosal membrane infection is caused by a virus.

The virus may be a Herpes Simplex Virus. Preferably, the virus is Herpes Simplex Virus 1 or Herpes Simplex Virus 2.

In another aspect, the present invention provides use of a composition of the first aspect in the manufacture of a medicament for the treatment of a skin or mucosal membrane infection.

In a further aspect, the present invention provides a composition of the first aspect for use in the treatment of a skin or mucosal membrane infection.

BRIEF DESCRIPTION OF THE FIGURES

FIG. 1 is a table showing the formulation of the composition in Examples 1 and 5 disclosed herein.

FIG. 2 is a table showing the formulation of the composition in Examples 2, 6 and 7 disclosed herein.

FIG. 3 is a table showing the terpene/essential oil formulation of the composition in Example 3 disclosed herein.

FIG. 4 is a table showing the formulations of the compositions in Example 4 disclosed herein.

DETAILED DESCRIPTION OF AN EMBODIMENT OF THE INVENTION

Copper is known to possess antimicrobial and antiviral properties (eg, Sagripanti et al. (1997) Mechanism of Copper-Mediated Inactivation of Herpes Simplex Virus. *Antimicrobial Agents and Chemotherapy* 41(4): 812-817; Borkow and Gabbay (2009) Copper, an ancient remedy returning to fight microbial, fungal and viral infections. *Curr. Chem. Biol.* 3: 272-278). However, high concentrations of copper may cause blood poisoning which can potentially be fatal. Moreover, copper is prone to precipitation and, as such, is often formulated with relatively large volumes of water. In contrast, the present inventors have surprisingly found that compositions comprising copper and a terpene or terpenoid compound, in addition to glycerol, a surfactant and an alcohol, can be formulated with little or no water and that such compositions are effective in the treatment of skin and mucosal membrane infections. Accordingly, compositions of the present invention comprise:
glycerol;
at least one surfactant;
an alcohol;
a terpene or terpenoid compound; and
a copper compound.

A number of different copper compounds may be used in accordance with the present invention. The copper compound may be a copper (I) compound or a copper (II) compound. In one or more embodiments, the copper compound is copper gluconate, copper carbonate, copper sulphate, copper chloride or copper salicylate. Preferably, the copper compound is copper sulphate and, more preferably, copper sulphate pentahydrate.

The composition may comprise from about 1% to about 10% by weight of the copper compound. Preferably, the composition comprises less than about 5% of the copper compound, such as from about 2% to about 4% by weight of the copper compound and, preferably, about 3% by weight of the copper compound.

The composition preferably includes a skin protectant such as glycerol. Glycerol may form a barrier over the skin and protect against irritation caused by touching, scratching, rubbing and the like. It may also provide a protective barrier over the lesion, preventing loss of the active ingredient. In one or more embodiments, the composition comprises at least 20% by weight of glycerol, such as at least 30% by weight, at least 35% by weight, at least 40% by weight, at least 45% by weight or, more preferably, at least 50% by weight of glycerol.

The composition preferably includes a terpene or terpenoid compound. Terpenes and terpenoids are diverse classes of organic compounds that are widespread in nature, particularly in plants, plant parts or plant oils, from which they may be extracted. Terpenes and terpenoids can also be synthesised. Terpenes and terpenoids have been shown to possess antimicrobial properties (eg, Chaumont and Leger (1992) Campaign Against Allergic Moulds in Dwellings, Inhibitor Properties of Essential Oil Geranium "Bourbon" Citronellol, Geraniol and Citral. *Ann. Pharm. Fr.* 50(3): 156-166; Mikhlin et al. (1983) Antifungal and Antimicrobial Activity of Some Derivatives of Beta-Ionone and Vitamin A. *Prikl Biokhim Mikrobiol* 19: 795-803; Kim et al. (1995) Antibacterial Activity of Some Essential Oil Components Against Five Foodborne Pathogens. *J. Agri. Food Chem.* 43: 2839-2845; Isman (2000) Plant essential oils for pest and disease management. *Crop Protection.* 19: 603-608). They have also been associated with the effective treatment of tumors (eg, Crowell et al. (1996) Antitumorigenic Effects of Limonene and Perillyl Alcohol Against Pancreatic and Breast Cancer. *Adv. Exp. Med. Biol.* 401: 131-136) and the lowering of cholesterol levels (eg, Elson et al. (1994) The Chemoprevention of Cancer by Melavonate-Derived Constituents of Fruits and Vegetables. *J. Nutr.* 124: 607-614).

The building block of terpenes and terpenoids is the C-5 hydrocarbon, isoprene ($C_5H_8$). The isoprene building blocks may be joined in a head-to-tail arrangement, thereby forming linear or branched chains, or they may be arranged as a ring. Whereas terpenes are generally hydrocarbons, terpenoids often contain additional functional groups. Terpenoids may result from the modification of a terpene such as when a methyl group has been moved or removed, or when an oxygen or other functional group has been added. However, the term "terpene" is often used interchangeably with the term "terpenoid".

The terpene or terpenoid compound may be present in, or extracted from, an essential oil. Essential oils are typically extracted from plants, or plant parts, and may comprise a volatile mixture of esters, alcohols, vitamins, aldehydes, ketones, terpenes and terpenoids. They are usually hydrophobic and immiscible in water. They may, however, be soluble in certain oils and organic solvents such as alcohols or acetone. Essential oils for use in the present invention may be extracted from, for example, a camphor laurel tree, a kapur tree, a rosemary plant, a mint plant, a eucalyptus tree or a tea tree. Other sources of essential oils may include Plantago (eg, *Plantago major*), Hypericum (eg, *Hypericaceae perforatus*), Baptisia, Calendula (eg, *Calendular officinalis*), myrrh, echinacea (eg, *Echinaceae angustifoliae radix* or *Echinaceae purpurea*), Phytolaca, Salvia, Tsuga, Styrax, Catechu black, Krameria, Crataegus, Glycerrhiza (eg, *Glycerrhiza glabra*), Angelica, Krameria, Matricaria, Mallow, sage, chamomile, Hammamelis, aloe vera, nettle. Kava Kava, Noni fruit (*Morinda citrifolia*), Feverfew (eg, *Tanacetum parthenolide*), Astragulus, cinnamon, cajeput, fennel, geranium, girofle, lavender, lemon, myrte, oregano, pine, sarriette, thyme, Pinus, Star anise and garlic.

Terpenes that may be suitable for use in accordance with the present invention include, for example, hemiterpenes, monoterpenes, sesquiterpenes, diterpenes, sesterterpenes, triterpenes, sesquarterpenes, tetraterpenes and polyterpenes. Terpenoids that may be suitable for use in accordance with the present invention include, for example, hemiterpenoids, monoterpenoids, sesquiterpenoids, diterpenoids, sesterterpenoids, triterpenoids, tetraterpenoids and polyterpenoids. In one or more embodiments, the terpene or terpenoid compound of the present invention is camphor ($C_{10}H_{18}O$). Camphor may be synthesised or it may be extracted from a plant oil such as the oil of the camphor laurel tree (*Cinnamomum camphora*), the kapur tree or rosemary (*Rosmarinus officinalis*). The camphor is preferably provided in a powder or granulated form such as tablets. In further embodiments, the terpene or terpenoid compound is menthol ($C_{10}H_{20}O$). Menthol may be synthesised or it may be extracted from a plant oil such as the oil of mint.

Compositions of the present invention preferably comprise between about 0.5% and 5% of the terpene or terpenoid compound by weight. Preferably, the composition comprises between about 1% and 4%, between about 1.5% and 3.5%, between about 2% and 3.5% or, more preferably, about 3% of the terpene or terpenoid compound by weight.

Those skilled in the art will understand that a variety of different alcohols may be used in accordance with the present invention. In one or more embodiments, the alcohol is a $C_1$-$C_8$ alcohol and, preferably, a $C_1$-$C_3$ alcohol. The alcohol may, for example, be ethanol or, preferably, isopropyl alcohol. The alcohol may be present in the composition in an amount of between about 10% and 50% by weight, such as between about 20% and 45% by weight or between about 25% and 40% by weight. Preferably, the alcohol is present at a concentration of about 35% by weight.

The composition preferably comprises a surfactant, and in some embodiments, more than one surfactant. A surfactant is a surface active agent that can act to stabilise an emulsion. Surfactants typically comprise a molecule having a polar or charged, hydrophilic head group and a hydrophobic tail group. Those skilled in the art will understand that compositions of the present invention may be formulated using one or more of a variety of surfactants. The surfactant may be an ionic, non-ionic or zwitterionic surfactant. Surfactants suitable for use in the compositions of the present invention may include anionic, cationic, amphoteric and non-ionic surfactants. Non-limiting examples of anionic surfactants include sulfate esters, sulfonate esters, phosphate esters and alkyl carbolates. Non-limiting examples of cationic surfactants include quaternary ammonium compounds, such as cetyl trimethylammonium bromide, cetylpyridinium chloride, benzethonium chloride and dioctadecyldimethylammonium bromide. Non-limiting examples of amphoteric surfactants include betaines, imino acetates and imino propionates. Non-limiting examples of non-ionic surfactants include fatty alcohols, glucosides, maltosides, polyethoxylated tallow amines, cocoamides, sorbitan alkyl esters, block copolymers of polyethylene glycol and polypropylene glycol, ethoxylated amines and ethoxylated alcohols. The composition of the present invention may comprise between about 1% and 10% by weigh of a surfactant such as between about 3% and 9% by weight or between about 4% and 8% by weight of a surfactant.

In one or more embodiments, the composition of the present invention comprises polysorbate 80 and polyethylene glycol 400 (PEG400). Preferably, the composition comprises polysorbate 80 at a concentration of between about 0.05% and 1% by weight such as between about 0.1% and 0.5% by weight. Preferably, the composition comprises polysorbate 80 at a concentration of about 0.2% by weight. The composition may also comprise PEG400 at a concentration of between about 1% and 10% by weight such as between about 2% and 7% by weight or between about 4% and 6% by weight. Preferably, the composition comprises PEG400 at a concentration of about 5% by weight.

In one embodiment, the composition for treating a skin or mucosal membrane infection of the present invention comprises:
  glycerol in an amount of between about 30% and 80% by weight;
  at least one surfactant in an amount of between about 1% and 10% by weight;
  an alcohol in an amount of between about 20% and 60% by weight;
  a terpene or terpenoid compound in an amount of between about 0.5% and 5% by weight; and
  a copper compound in an amount of between about 1% and 10% by weight.

In another embodiment, the composition for treating a skin or mucosal membrane infection of the present invention comprises:
  glycerol in an amount of between about 30% and 60% by weight;
  at least one surfactant in an amount of between about 1% and 10% by weight;
  an alcohol in an amount of between about 20% and 50% by weight;
  a terpene or terpenoid compound in an amount of between about 0.5% and 10% by weight; and
  a copper compound in an amount of between about 1% and 5% by weight.

In another embodiment, the composition for treating a skin or mucosal membrane infection of the present invention comprises:
  glycerol in an amount of at least about 35% by weight;
  at least one surfactant in an amount of between about 1% and 10% by weight;
  an alcohol in an amount of between about 10% and 50% by weight;
  a terpene or terpenoid compound in an amount of between about 0.5% and 5% by weight; and
  a copper compound in an amount of between about 1% and 5% by weight.

In another embodiment, the composition comprises:
glycerol in an amount of at least about 40% by weight;
at least one surfactant in an amount of between about 3% and 7% by weight;
an alcohol in an amount of between about 25% and 40% by weight;
a terpene or terpenoid compound in an amount of between about 1% and 4% by weight; and
a copper compound in an amount of between about 2% and 4% by weight.

In a further embodiment, the composition comprises:
glycerol in an amount of at least about 40% by weight;
at least one surfactant in an amount of about 5% by weight;
an alcohol in an amount of about 35% by weight;
a terpene or terpenoid compound in an amount of about 3% by weight; and
a copper compound in an amount of about 3% by weight.

The composition may further comprise one or more herbal extracts such as *Hypericum perforatum* and/or *Calendula officinalis* extract. *Hypericum perforatum* and *Calendula officinalis* extracts have antimicrobial and antiviral activity (Clewell et al. Efficacy and tolerability assessment of a topical formulation containing sulfate and *Hypericum perforatum* on patients with herpes skin lesions: a comparative, randomized controlled trial. *Journal of Drugs in Dermatology* 11(2): 209-215; Wölfe et al. Topical application of St. John's Wort (*Hypericum perforatum*). *Planta Med.* 80: 109-120; Roveroni-Favaretto et al. Topical *Calendula officinalis* L. successfully treated exfoliative cheilitis: a case report. *Cases Journal.* 2: 9077) and can be obtained from various parts of the plant, including flowers, leaves, seeds, roots and stems. The extracts can be prepared using distillation, pressing, or solvent (eg, ethanol) extraction. In one or more embodiments, the *Hypericum perforatum* extract is present in the composition at a concentration of about 1% by weight or less such as about 0.5% by weight or less, 0.25% by weight or less or 0.1% by weight or less. Preferably, the *Hypericum perforatum* extract is present in the composition at a concentration of about 0.05% by weight. In one or more embodiments, the *Calendula officinalis* extract is present in the composition at a concentration of about 1% by weight or less such as about 0.5% by weight or less, 0.25% by weight or less or 0.1% by weight or less. Preferably, the *Calendula officinalis* extract is present in the composition at a concentration of about 0.05% by weight.

In one embodiment, the composition comprises:
glycerol in an amount of at least about 40% by weight;
at least one surfactant in an amount of about 5% by weight;
an alcohol in an amount of about 35% by weight;
a terpene or terpenoid compound in an amount of about 3% by weight;
a copper compound in an amount of about 3% by weight; and
*Hypericum perforatum* extract in an amount of between about 0.01% and 2% by weight.

In a further embodiment, the composition comprises:
glycerol in an amount of at least about 40% by weight;
at least one surfactant in an amount of about 5% by weight;
an alcohol in an amount of about 35% by weight;
a terpene or terpenoid compound in an amount of about 3% by weight;
a copper compound in an amount of about 3% by weight;
*Hypericum perforatum* extract in an amount of between about 0.01% and 2% by weight; and
*Calendula officinalis* extract in an amount of between about 0.01% and 2% by weight.

In one or more embodiments, the composition of the present invention includes Vitamin E. Vitamin E may be present in, or extracted from, an essential oil. The vitamin E is preferably present at a concentration of 1% or less by weight, 0.5% or less by weight or 0.25% or less by weight. Preferably, the vitamin E is present at a concentration of about 0.1% by weight.

In some embodiments, the composition further comprises aloe vera. Aloe vera is obtained from plants of the genus *Aloe*, such as *Aloe barbadensis* plants. In one or more embodiments, the aloe vera is present in the composition at a concentration of about 1% by weight or less, about 0.5% or less by weight, about 0.25% or less, about 0.1% or less by weight, about 0.05% or less by weight or about 0.025% or less by weight. Preferably, the aloe vera is present at a concentration of about 0.01% by weight.

In one embodiment, the composition comprises:
glycerol in an amount of between about 30% and 80% by weight;
at least one surfactant in an amount between about 1% and 10% by weight;
an alcohol in an amount between about 20% and 60% by weight;
a terpene or terpenoid compound in an amount between about 0.5% and 5% by weight;
a copper compound in an amount between about 1% and 10% by weight;
*Hypericum perforatum* extract in an amount of between about 0.01% and 2% by weight;
*Calendula officinalis* extract in an amount of between about 0.01% and 2% by weight;
vitamin E in an amount of between about 0.01% and 2%; and
aloe vera in an amount of between about 0.01% and 2%.

The present inventors have surprisingly found that compositions of the present invention can be prepared with no, or substantially no, water. Accordingly, the composition may be a non-aqueous composition. The compositions were observed to form stable, homogenous mixtures. The composition may be stable for at least 3 months, such as for 6 months, 9 months, 12 months, 15 months, 18 months or 21 months. Preferably, the composition is stable for 24 months.

In one or more embodiments, the composition of the present invention has a pH of less than about 7, such as less than about 6, less than about 5, less than about 4 or less than about 3. The pH of the composition may be between about 1 and 4 or between about 1.5 and 3.5. Preferably, the pH of the composition is between about 2 and 2.5.

In one or more embodiments, the composition of the present invention has a density (SG) of between about 0.25 g/mL and 2 g/mL, such as between about 0.5 g/mL and 1.5 g/mL or between about 0.75 g/mL and 1.25 g/mL. Preferably, the density of the composition is between about 1 g/mL and 1.1 g/mL.

In one or more embodiments, the composition of the present invention has a viscosity of between about 100 cps and 500 cps, such as between about 150 cps and 400 cps or between about 200 cps and 350 cps. Preferably, the viscosity of the composition is between about 225 cps and 300 cps.

The composition may comprise further ingredients that are suitable for the topical treatment of skin or mucosal membrane infections. For example, the composition may further comprise, inter alia, preservatives, thickeners, osmotic regulators, flavours, fragrances, emollients, humectants, colorants pigments or pharmaceutically acceptable carriers. The composition may also comprise stabilisers such as propylene glycol which may be present at a concentration of between about 5% and 25% by weight or, preferably, between about 10% and 20% by weight.

In preferred embodiments, the composition is a homogenous composition. The composition is preferably suitable for topical formulation. The composition may be formulated as a cream, a lotion, a paste, an emollient, a gel, a foam or an emulsion.

The term "emulsion" as used herein includes droplets, dispersions or other structures that form when two or more immiscible liquids are combined. An emulsion may be prepared by simple stirring and without the use of high shear mixers. Alternatively, emulsions having smaller droplet sizes may be prepared using high pressures and/or high shear forces. Microemulsions generally comprise droplets having a diameter range from about 1000 nm to about 500 urn. Nanoemulsions, on the other hand, comprise smaller droplets with a diameter of less than about 1000 nm.

The composition may be used to treat a skin or mucosal membrane infection, and preferably, a viral infection. The infection may be caused by a poxvirus, a herpesvirus or a human papillomavirus. In some embodiments, the viral infection is caused by herpes simplex virus, herpes zoster virus, *Molluscuum contagiosum*, human papillomavirus, polio virus, shingles-associated viruses, varicella zoster virus, chicken pox-associated viruses or human immunodeficiency virus. Preferably, the viral infection is caused by herpes simplex virus.

Those skilled in the art will understand that the compositions of the present invention are also useful for treating other skin or mucosal membrane infections. For example, the composition may be used to treat a fungal infection, such as tinea. The form of tinea may be, for example, tinea pedis, tinea corporis, tinea manuum, tinea cruris, tinea barbae or tinea capitis.

The term "pharmaceutically acceptable" as used herein refers to substances that do not cause substantial adverse allergic or immunological reactions when administered to a subject. A "pharmaceutically acceptable carrier" includes, but is not limited to, solvents, coatings, dispersion agents, wetting agents, isotonic and absorption delaying agents and disintegrants.

The term "substantially no" as used in reference to water content means that water constitutes less than about 2% by weight such as less than 1% by weight, preferably less than 0.5% by weight or, more preferably, less than 0.1% by weight.

The terms "comprise", "comprises", "comprised" or "comprising", "including" or "having" and the like in the present specification and claims are used in an inclusive sense, ie, to specify the presence of the stated features but not preclude the presence of additional or further features.

In the context of this specification the term "about" is understood to refer to a range of +/−10%, preferably +/−5% or +/−1% or, more preferably, +/−0.1%.

In the context of this specification the terms "a" and "an" are used herein to refer to one or to more than one (i.e at least one) of the grammatical object of the article. By way of example, "an element" means one element or more than one element.

Example 1

A composition suitable for treating a skin or mucosal membrane infection was prepared as set out in FIG. 1.

Example 2

A composition suitable for treating a skin or mucosal membrane infection was prepared as set out in FIG. 2.

In addition to the composition shown in FIG. 2, compositions comprising between 1% and 4% camphor and between 1% and 5% cupric sulphate were also prepared. The compositions formed a stable, homogenous mixture.

Example 3

Additional compositions, based on that shown in FIG. 2, were produced in which camphor was replaced with the alternative terpene/terpenoid compounds or essential oils shown in FIG. 3.

Example 4

Further compositions suitable for treating a skin or mucosal membrane infection were prepared as set out in FIG. 4.

The compositions formed a stable, homogenous mixture.

Example 5

The composition shown in FIG. 1 was prepared by the following step-wise process:

Step 1
Glycerol and cupric sulphate pentahydrate were mixed until completely dissolved. To assist dissolution, the mixture was heated to 80° C. If particulate matter was observed, it was removed by filtration.

Step 2
Camphor tablets were ground into a powder and dissolved in isopropyl alcohol.

Step 3
PEG400, polysorbate 80 and vitamin E were combined to form a homogenous mixture.

The compositions produced by steps 1 to 3 were combined and mixed until homogenous. Further glycerol was added as appropriate. To avoid isopropyl alcohol loss, the final composition was stored in a sealed container at a temperature of below 25° C.

Example 6

The composition shown in FIG. 2 was prepared by the following step-wise process:

Step 1
Glycerol, cupric sulphate pentahydrate and aloe vera were mixed until completely dissolved. To assist dissolution, the mixture was heated to 80° C. If particulate matter was observed, it was removed by filtration.

Step 2
Camphor tablets were ground into a powder and dissolved in isopropyl alcohol.

Step 3
PEG400, polysorbate 80, vitamin E, *Hypericum perforatum* extract and *Calendula officinalis* extract were combined to form a homogenous mixture.

The compositions produced by steps 1 to 3 were combined and mixed until homogenous. Further glycerol was added as appropriate. To avoid isopropyl alcohol loss, the final composition was stored in a sealed container at a temperature of below 25° C.

Example 7

A composition based on that described in Example 2 was prepared as a 10 kg batch. 0.5 mL aliquots were prepared for stability testing. Each aliquot was stored in a clear glass vial at 30° C./65% relative humidity. The composition formed a homogenous mixture with a pH of between about 1.5 and 3.5, a density (SG) of between about 1 g/mL and 1.1 g/mL, and a viscosity of between about 225 cps and 300 cps (S#3, 12 rpm, at 20° C.) which was stable for more than 12 months.

Although the invention has been described with reference to specific embodiments, it will be appreciated by those skilled in the art that the invention may be embodied in many other forms.

The invention claimed is:

1. A method of treating a skin or mucosal membrane infection, the method comprising topically applying a composition to the skin or mucosal membrane infection, the composition comprising:
    glycerol in an amount of between about 30% and 80% by weight,
    at least one surfactant in an amount of between about 1% and 10% by weight,
    an alcohol in an amount of between about 20% and 60% by weight,
    a terpene or terpenoid compound in an amount of between about 0.5% and 10% by weight, and
    a copper compound in an amount of between about 1% and 10% by weight, and
    the composition comprises substantially no water.

2. The method of claim 1 wherein the skin or mucosal membrane infection is caused by a bacterium, a virus or a fungus.

3. The method of claim 2 wherein the skin or mucosal membrane infection is caused by a virus.

4. The method of claim 3 wherein the virus is a Herpes Simplex Virus.

5. The method of claim 4 wherein the virus is Herpes Simplex Virus 1 or Herpes Simplex Virus 2.

6. The method of claim 1 wherein the terpene or terpenoid compound is present in or extracted from an essential oil.

7. The method of claim 6 wherein said essential oil is obtained from a camphor laurel tree, a kapur tree, a rosemary plant, a mint plant, a eucalyptus tree or a tea tree.

8. The method of claim 1 wherein the terpene or terpenoid compound is camphor.

9. The method of claim 1 wherein the terpene or terpenoid compound is menthol.

10. The method of claim 1 wherein the copper compound is selected from the group consisting of copper gluconate, copper carbonate, copper sulphate, copper chloride and copper salicylate.

11. The method of claim 10 wherein the copper compound is copper sulphate.

12. The method of claim 11 wherein the copper sulphate is copper sulphate pentahydrate.

13. The method of claim 1 wherein the alcohol is isopropyl alcohol.

14. The method of claim 1 further comprising *Hypericum perforatum* extract.

15. The method of claim 1 further comprising *Calendula officinalis* extract.

16. The method of claim 1 further comprising aloe vera.

17. The method of claim 1 further comprising vitamin E.

18. The method of claim 1 wherein the at least one surfactant comprises polyethylene glycol.

19. The method of claim 1 wherein the at least one surfactant comprises polysorbate 80.

20. The method of claim 1 wherein the composition comprises:
    the glycerol in an amount of between about 30% and 60% by weight;
    the alcohol in an amount of between about 20% and 50% by weight;
    the terpene or terpenoid compound in an amount of between about 0.5% and 5% by weight; and
    the copper compound in an amount of between about 1% and 5% by weight.

21. A method of treating a skin or mucosal membrane infection, the method comprising topically applying a composition to the skin or mucosal membrane infection,
    wherein the composition comprises:
    glycerol in an amount of at least about 35% by weight;
    at least one surfactant in an amount of between about 1% and 10% by weight;
    an alcohol in an amount of between about 10% and 50% by weight;
    a terpene or terpenoid compound in an amount of between about 0.5% and 5% by weight; and
    a copper compound in an amount of between about 1% and 5% by weight,
    wherein the composition comprises substantially no water.

22. The method of claim 21 wherein the composition comprises:
    the glycerol in an amount of at least about 40% by weight;
    the at least one surfactant in an amount of between about 3% and 7% by weight;
    the alcohol in an amount of between about 25% and 40% by weight;
    the terpene or terpenoid compound in an amount of between about 1% and 4% by weight; and
    the copper compound in an amount of between about 2% and 4% by weight.

23. The method of claim 21 wherein the composition comprises:
    the glycerol in an amount of at least about 40% by weight;
    the at least one surfactant in an amount of about 5% by weight;
    the alcohol in an amount of about 35% by weight;
    the terpene or terpenoid compound in an amount of about 3% by weight;
    the copper compound in an amount of about 3% by weight; and
    *Hypericum perforatum* extract in an amount of between about 0.01% and 2% by weight.

24. The method of claim 21 wherein the composition comprises:
    the glycerol in an amount of at least about 40% by weight;
    the at least one surfactant in an amount of about 5% by weight;
    the alcohol in an amount of about 35% by weight;
    the terpene or terpenoid compound in an amount of about 3% by weight;
    the copper compound in an amount of about 3% by weight;
    *Hypericum perforatum* extract in an amount of between about 0.01% and 2% by weight; and
    *Calendula officinalis* extract in an amount of between about 0.01% and 2% by weight.

25. A method of treating a skin or mucosal membrane infection, the method comprising topically applying a composition to the skin or mucosal membrane infection, wherein the composition comprises:
    glycerol in an amount of between about 30% and 80% by weight;

at least one surfactant in an amount between about 1% and 10% by weight;
an alcohol in an amount between about 20% and 60% by weight;
a terpene or terpenoid compound in an amount between about 0.5% and 5% by weight;
a copper compound in an amount between about 1% and 10% by weight;
*Hypericum perforatum* extract in an amount of between about 0.01% and 2% by weight;
*Calendula officinalis* extract in an amount of between about 0.01% and 2% by weight;
vitamin E in an amount of between about 0.01% and 2%; and
aloe vera in an amount of between about 0.01% and 2%, wherein the composition comprises substantially no water.

* * * * *